(12) United States Patent
Asada et al.

(10) Patent No.: US 8,859,853 B2
(45) Date of Patent: Oct. 14, 2014

(54) CAPSULES CONTAINING VITAL CELLS OR TISSUES

(75) Inventors: Masanori Asada, Osaka (JP); Yumi Hatano, Osaka (JP); Ryosei Kamaguchi, Osaka (JP); Hideki Sunohara, Osaka (JP)

(73) Assignee: Morishita Jintan Co., Ltd, Osaka (JP)

( * ) Notice: Subject to any disclaimer, the term of this patent is extended or adjusted under 35 U.S.C. 154(b) by 1459 days.

(21) Appl. No.: 11/210,424

(22) Filed: Aug. 24, 2005

(65) Prior Publication Data

US 2005/0283849 A1    Dec. 22, 2005

Related U.S. Application Data

(62) Division of application No. 10/480,720, filed as application No. PCT/JP01/05606 on Jun. 28, 2001, now Pat. No. 6,982,095.

(51) Int. Cl.

| | |
|---|---|
| *A01H 5/10* | (2006.01) |
| *A01H 4/00* | (2006.01) |
| *A61K 35/74* | (2006.01) |
| *C12N 1/20* | (2006.01) |
| *A23C 11/10* | (2006.01) |
| *A23L 1/03* | (2006.01) |
| *A23L 1/00* | (2006.01) |
| *A23L 2/38* | (2006.01) |
| *C12N 1/04* | (2006.01) |
| *A61K 36/00* | (2006.01) |
| *A23L 1/30* | (2006.01) |

(52) U.S. Cl.
CPC ....... *C12N 1/20* (2013.01); *A01H 4/003* (2013.01); *A61K 35/742* (2013.01); *A61K 35/745* (2013.01); *A23Y 2300/55* (2013.01); *A01H 4/006* (2013.01); *A23C 11/106* (2013.01); *A23L 1/0345* (2013.01); *A01H 4/00* (2013.01); *A23L 1/0029* (2013.01); *A23L 2/38* (2013.01); *C12N 1/04* (2013.01); *A23Y 2220/00* (2013.01); *A61K 36/00* (2013.01); *A23L 1/3014* (2013.01)
USPC ............. 800/298; 428/402; 428/402.21

(58) Field of Classification Search
None
See application file for complete search history.

(56) References Cited

U.S. PATENT DOCUMENTS

| 4,562,663 A | * | 1/1986 | Redenbaugh ................. 800/295 |
| 4,814,274 A | | 3/1989 | Shioya et al. |
| 4,857,465 A | * | 8/1989 | Barwale et al. ............... 800/276 |
| 5,040,960 A | | 8/1991 | Shioya et al. |
| 5,138,793 A | | 8/1992 | Florin et al. |
| 5,232,712 A | | 8/1993 | Mills et al. |
| 5,250,082 A | * | 10/1993 | Teng et al. ..................... 47/57.6 |
| 5,330,835 A | | 7/1994 | Kikuchi et al. |
| 5,382,269 A | * | 1/1995 | Giroud-Abel et al. ......... 47/57.6 |
| 5,771,632 A | * | 6/1998 | Liu et al. ...................... 800/295 |
| 5,807,724 A | * | 9/1998 | Resnick ....................... 435/177 |

FOREIGN PATENT DOCUMENTS

| EP | 141374 A1 | 5/1985 |
| EP | 408922 A1 | 10/1991 |
| EP | 0573978 | 12/1993 |
| EP | 0634167 | 1/1995 |
| FR | 2650758 | 2/1991 |
| JP | 61-151127 | 7/1986 |
| JP | 62-263128 | 11/1987 |
| JP | 1-228456 | 9/1989 |
| JP | 3-155722 | 7/1991 |
| JP | 5-31352 | 7/1994 |
| JP | 8-242763 | 9/1996 |
| JP | 62-186779 | 8/1997 |
| JP | 63-246333 | 10/1998 |
| WO | 9101803 | 2/1991 |
| WO | 9833375 | 8/1998 |

OTHER PUBLICATIONS

Hideki Sunohara, Food Processing Technology, vol. 15, pp. 28-33 (1995) Japan.
Masanori Asada, Bioscience and Industry vol. 58, pp. 31-34, (2000) Japan.
International Search Report, PCT/JP01/05606, Sep. 4, 2001.
Supplementary European Search Report for PCT/JP2001/05606, dated Mar. 8, 2006.
Redenbaugh, et al. Somatic Seeds: Encapsulation of Asexual Plant Embryos, Bio/Technology, vol. 4, pp. 797-801, Sep. 1986.
Murashige. The Impact of Plant Tissue Culture on Agriculture, In Thorpe, T. (Ed.), Frontiers of Plant Tissue Culture, University of Calgary, Calgary, pp. 15-26, 1978.
Kamaguchi et al, "An Innovative Technology Utilizing Interfacial Tension for Multi-layer Seamless-capsule Applicable to Pharmaceutical Products", Pharm Tech Japan, vol. 15, No. 12, pp. 1817-1830, 1999.

* cited by examiner

*Primary Examiner* — Lora E Barnhart Driscoll
(74) *Attorney, Agent, or Firm* — Amin, Turocy & Watson, LLP

(57) ABSTRACT

Artificial seeds formed of a seamless soft capsule are provided herein. The artificial seed contains a meristematic plant cell or tissue. The artificial seed has a structure of three or more layers containing an innermost layer, an inner layer covering the innermost layer, and an outer layer covering the inner layer. The innermost layer can contain an aqueous liquid, the inner layer can be formed by an inner membrane containing hardened oil, and the outer layer can be formed of a biodegradable outer membrane.

15 Claims, 1 Drawing Sheet

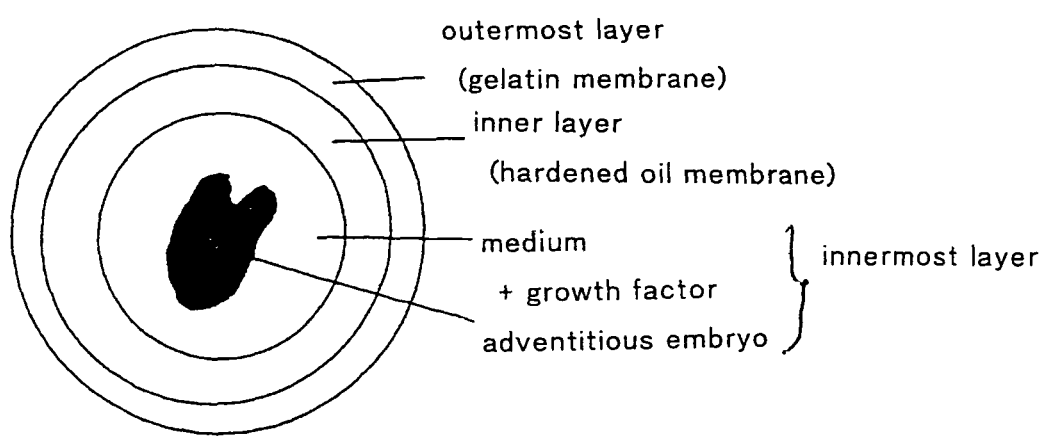

CAPSULES CONTAINING VITAL CELLS OR TISSUES

CROSS REFERENCE TO RELATED APPLICATION

This application is a divisional of U.S. application Ser. No. 10/480,720, entitled Capsules Containing Vital Cells or Tissues and filed on Dec. 12, 2003 now U.S. Pat. No. 6,982,095, the entirety of which is incorporated herein by reference.

TECHNICAL FIELD

The present invention relates to capsules including living (vital) cells or tissues and applications thereof. More specifically, the present invention relates to capsules that include living cells or tissues derived from microorganisms, plants or animals as the inclusion and in which these cells or tissues can be grown. The present invention also relates to foods containing such capsules and artificial seed capsules having excellent storage stability and containing redifferentiable plant cell tissues that germinate rapidly when being sown in soil.

BACKGROUND ART

Fermented foods obtained by allowing microorganisms to act on foods have been eaten since old times. Yogurt, which is a typical fermented food, is obtained by allowing lactic bacteria, *bifidobacteria* or the like (hereinafter, unless otherwise indicated, they are collectively abbreviated as "lactic bacteria") to act on milk. When yogurt is ingested, lactic bacteria are delivered to the intestines, act actively in the intestines and actively improve intestinal disorders. However, since most of lactic bacteria die in the stomach due to their strong acidity, only a few living lactic bacteria can reach the intestine.

In order to solve this problem, it has been attempted to include lactic bacteria in an enteric capsule to deliver the lactic bacteria to the intestines (for example, Japanese Laid-Open Patent Publication No. 8-242763).However, the lactic bacteria included in the capsule are freeze-dried and it takes a long time until the freeze-dried lactic bacteria absorb water and exhibit their activities again.

If living cells can be delivered to the intestines, the living cell can exhibit their activities immediately and sufficiently. Therefore, there is a demand for a technique for delivering living cells to the intestines.

On the other hand, the remarkable advance of biotechnology has affected various fields such as development of pharmaceuticals or improvement of plants. In the field of plants, there have been attempts to produce artificial seeds from redifferentiable plant cell tissues (hereinafter, referred to simply as "cell tissues"). In general, to produce artificial seeds, at first, cell tissues are dispersed or suspended in a solution of polysaccharides, low molecular weight of polymeric substance or crosslinkable polymer. Then this dispersion or suspension is gelled so that the cell tissues are enclosed in gels, followed by being molded into a form of a bead, a plate, a bar or a fiber.

However, the artificial seeds in which cell tissues are enclosed in gels as described above have no tolerance with respect to dryness when left at a room temperature. Therefore, such artificial seeds have to be sown within four days after they are prepared. In addition, these artificial seeds cannot be stored even for one month, unless they are not stored in a refrigerator or a liquid in order to prevent them from being dried. Thus it is difficult to store them in a dry place, such as a barn of a farmer or a storehouse, without a special refrigerating facility.

In order to improve this dryness problem, it has been attempted to cover the surface of the gels with paraffin, wax or the like. It is possible to improve the storage stability by covering the surface of the gels. However, since paraffin or wax is stable and is hardly degraded, the artificial seeds covered with paraffin or wax cannot germinate when they are sown in soil. Therefore, it is necessary to make an opening for each artificial seed when sowing, which is inconvenient. Thus such artificial seeds cannot be used practically.

As described above, there is a demand for a technique to enclose living cells and grow the living cells. Such technique can be applied not only in a field of food chemistry, but also to a wide range of fields, for example, pharmaceutical or agricultural field. In particular, in the field of the artificial seeds, there is a demand for artificial seeds that can be stored for at least three months in a dry place without a special refrigerating facility, and can germinate in a few days when being sown in soil. If such artificial seeds can be obtained, this technique can actually be applied to a wide range of fields, for example, agriculture, forestry, horticulture and floriculture, in combination with a technique for cultivating plant cell tissues, a cloning technique or a virus-free technique.

DISCLOSURE OF INVENTION

The inventors of the present invention conducted in-depth research in order to solve the above problem. Consequently the present inventors found that a capsule that includes living cells or tissues suspended in a liquid can be produced, and that this can be applied to the fields of foods and agriculture and thus achieved the present invention.

The present invention provides a capsule including a liquid in which living cell or tissue is suspended, wherein the cell or tissue can grow in the liquid.

In a preferable embodiment, the capsule is a seamless soft capsule.

In one preferable embodiment, the cell or the tissue is a cell or a plant tissue used for food.

In one preferable embodiment, the cell or the tissue is one or two or more cells or tissues selected from the group consisting of lactic acid bacteria (including *bifidobacteria*), *Bacillus natto*, baker's yeasts, brewer's yeasts, filamentous fungus for brewing, single cell algae, multicellular algae, edible plants, edible plant tissues and their freeze-dried bacteria or tissues.

The present invention also is directed to food containing the above-described capsule, and preferably the food containing the capsule is fruit juice beverages, vegetable juice, health drinks, processed milk, soybean milk, jelly, yogurt, lactic acid bacteria beverages, fermented milk, carbonated drinks, near water, and pudding.

Furthermore, the present invention is directed to an artificial seed including a redifferentiable plant cell tissue suspended in a liquid, wherein the tissue is preserved in the liquid.

Furthermore, the present invention is directed to an artificial seed formed of a seamless soft capsule having a structure of three or more layers comprising an innermost layer, an inner layer covering the innermost layer, and an outer layer covering the inner layer, wherein the innermost layer includes a redifferentiable plant cell tissue, wherein the inner layer is formed by an inner membrane comprising hardened oil as a main component, and wherein the outer layer is formed of a biodegradable outer membrane.

In one preferable embodiment, the outer membrane is dried.

In one preferable embodiment, the redifferentiable plant cell tissue is selected from the group consisting of adventitious embryos, adventitious buds, multiple shoots, shoot apices, growing points, protocorm-like bodies, adventitious roots, and capillary roots.

In one preferable embodiment, the inner membrane is microbiologically degradable hardened oil that is solid at room temperature.

In another preferable embodiment, the outer membrane is a microbiologically degradable outer membrane selected from the group consisting of protein, polysaccharides, and biodegradable plastics.

BRIEF DESCRIPTION OF DRAWINGS

FIG. 1 is a schematic cross-sectional view of an artificial seed of the present invention.

BEST MODE FOR CARRYING OUT THE INVENTION

Since it was difficult to capsulate aqueous substances, only dry cells were capsulated. It was thought to be impossible to grow the cells or the tissues that is enclosed in a capsule, and therefore, no attempts were made to include and grow the cells or tissues in a capsule. However, the inventors of the present invention succeeded in capsulating aqueous substances for the first time, and found that the cells or the tissues do not die and can grow even if they are enclosed in the aqueous substance in the capsule, and thus achieved the present invention.

The present invention can provide the following effect, for example. Conventionally, only freeze-dried lactic bacteria, *bifidobacteria* or the like could be delivered, so that only a moderate effect of improving intestinal disorders was obtained. On the contrary, by the present invention, an immediate and potent effect of improving intestinal disorders can be brought about by delivering living lactic bacteria, *bifidobacteria* or the like. Furthermore, since cells or tissues can grow in the capsules, capsules having a higher bacterium density (e.g., about $10^{10}$ to $10^{11}$/g of the capsule) can be obtained. Therefore, the present invention can be used in a wider range of applications such as bioreactors, pharmaceuticals, medicine, and artificial seeds, in addition to food application as described above.

In a preferable embodiment, the ratio of the liquid enclosed in the capsule (inner liquid) is about 30% by weight with respect to the total weight of the capsule. In this case, the bacterial cell density of the inner liquid becomes as high as $3.3 \times 10^{11}$/ml. Unless the bacterial cells are not included in the capsule, it is not possible to grow the bacterial cells to such a high density. Furthermore, when the bacterial cells are cultured and concentrated to such a high density, the viscosity of the bacterial cell suspension becomes very high. Therefore, it is very difficult to include such a high density of bacterial cell suspension into the capsule from the outside with current techniques, which proves the utility of the present invention more clear.

"Capsule" in the present specification refers to a structure that has an outer membrane and is able to enclose or include a liquid, a suspension or a culture solution containing cells or tissues within the outer membrane. The capsule generally has a spherical shape, but is not limited to the spherical shape.

As the outer membrane of the capsule, any membrane can be used, as long as it is conventionally used for capsules. As a membrane, membrane made of natural polymer or a synthetic polymer can be used. When it is used for food applications, a membrane made of natural polymer is preferable.

For the shape of the capsule, a two-layered structure can be used, and a three-layered structure or a structure having more layers can be used. A three-layered structure is preferable.

In the case of a three-layered structure, an innermost layer is a liquid containing living cells or tissues, an intermediate layer that covers the liquid of the innermost layer is a lipophilic membrane, and an outermost layer is an outer membrane. It is preferable that the outer membrane has one or more properties of edibility, easy to decompose (e.g., biodegradable), enteric properties, water-insolubility, and biocompatibility according to the application.

The innermost layer (inclusion) is a liquid such as a water, a physiological saline solution, a buffer, a culture medium and contains components necessary to grow or maintain the lives of the cells or tissues.

Hereinafter, at first, capsules used in food applications will be described, and then artificial seeds will be described.

For use in food applications, various oils and fats, fatty acids or fatty acid ester of saccharides that are edible can be used as a lipophilic membrane of the intermediate layer. Preferably, animal oils and fats, vegetable oils and fats, biologically or chemically treated oils and fats thereof can be used. Examples of edible oils and fats include, but are not limited to, various deep frying oils, salad oil, hardened oil having a melting point of 35° C. or less, vitamin E, wheat germ oil, sesame oil, cocoa butter, butter, margarine, shortening, and fatty acid ester of sucrose. By using these lipophilic materials, capsules enclosing aqueous substances can be obtained.

When the capsule of the present invention is used for food applications, as the edible outer membrane, natural polymer membrane such as gelatin, agar, pectin, alginic acid, carrageenan, curdlan, starch, gellant gum, glucomannan, or mixtures thereof can be used. Further, if desired, an edible polymer membrane obtained by adding a protein, a glycoprotein, a mucopolysaccharide, a saccharide, a sugar alcohol, a polyalcohol or the like to the above edible outer membrane is also preferable as the outer membrane. Specific examples of natural polymer include, but are not limited to, Arabian gum, pullulan, dextran, xanthan gum, Locust bean gum, collagen, and casein.

Furthermore, outer membranes that are soluble in the mouth, the stomach, the small intestine or the large intestine or outer membranes that are insoluble and discharged can be selected, if desired. The outer membrane that is soluble in the intestines, for example, can be obtained by combining gelatin or agar and pectin. For the outer membrane, glycerin can be added in view of the moldability.

In the case of a three-layered structure, examples of preferable combinations are shown, in the order of the intermediate layer (inner membrane)—the outermost layer, for example, vitamin E oil—agar, wheat germ oil—sodium alginate, a fatty acid ester of sucrose—gelatin, medium fatty acid ester of glycerin—carrageenan. Among these, vitamin E oil—2 to 4% agar and wheat germ oil—2 to 4% sodium alginate are preferable in term of the properties of the obtained capsule.

The constitution ratio of the inclusion (the innermost layer), the intermediate layer and the outermost layer depends on the size of the capsule, but is preferably 10 to 70:10 to 50:5 to 50 by weight, and more preferably 30 to 50:25 to 40:25 to 40.

The capsule of the present invention is preferably a seamless soft capsule. If the seamless capsule has a multi-layered structure, each of the intermediate layer and the outermost layer can be made thin. Thus, it seems that a substance that is necessary for growth of the cells or the tissues can be more easily moved between the inside and the outside of the capsule, thereby enabling the cells or the tissues in the capsule to grow. Furthermore, the grown cells cannot be leaked to the outside of the capsule.

Furthermore, depending on the application, the outermost layer can be a membrane having a large pore size, good permeability and a low mass transfer resistance, or a membrane having a small pore size, high barrier properties and a high mass transfer resistance. Moreover, a capsule having various functions can be prepared, for example, by adding a charged substance to the outer membrane so that the outer membrane have a selectivity for permeating a charged material.

There is no limitation regarding the cells or the tissues to be included in the capsule. Bacteria, yeasts, molds, algae, plant cells, plant or animal tissues can be used, depending on the application.

Examples of cells or plant tissues used in food applications include lactic bacteria (including *bifidobacteria*), *Bacillus natto*, baker's yeasts, brewer's yeasts (e.g., wine yeasts, sake yeasts, soybean yeasts, or soy sauce yeasts), filamentous fungus for brewing (e.g., *Aspergillus oryzae*), single cell algae (e.g., *Chlorella pyrenoidosa, Spirulina*), multicellular algae (e.g., *Undaria pinnatifida, tangle*), edible plants and edible plant tissues (e.g., ginseng).

The capsules including these cells or tissues can be produced by a method commonly used by those skilled in the art. When the capsule has a three-layered structure, it is most preferable to make a seamless soft capsule. A method for producing a seamless soft capsule is disclosed in, for example, Japanese Laid-Open Patent Publication No. 5-31352, Food Processing Technology vol. 15, pp. 28-33, 1995, or Bioscience and Industry, vol. 58, No. 7, pp. 31-34 (2000). In particular, it is more preferable to produce a seamless soft capsule with an oily substance (e.g., hardened oil) as the intermediate layer (inner membrane) using a dropping method with a triple tube nozzle.

The amount of the cells or tissues included in the capsule can range from the minimum amount that allows survival or growth to a cell density that can be achieved by culturing and collecting cells or tissues by filtration or centrifugation. However, in the present invention, since it is possible to increase the number of cells or tissues in the capsule to a high density, which is a feature of the present invention, the concentration of the cells or tissues to be inoculated in the capsule is sufficient as low as that of sub-cultivation level.

The average particle size of the seamless soft capsule depends on the application of the capsule. In general, the mean particle size is 0.1 mm to 10 mm, more preferably 0.2 to 8 mm. When the capsule is used for foods, the average particle size is preferably 4 mm or less, and more preferably 0.1 mm to 2 mm. Such a seamless soft capsule can be drunk smoothly as it is, however, in order to eat more smoothly, the surface of the capsule can be coated with a paste or a thickener such as starch, a hydrolyzed starch or pectin.

The living cells or tissues included in the seamless soft capsule can grow even in the capsule preferably by suspending the capsule in a suitable cultivation medium. In particular, in the case where a membrane material that requires multivalent metal ions for gel formation, such as alginate, is used as an outer membrane, it is preferable to add multivalent metal ions to the medium in a concentration necessary to maintain the gel intensity. Therefore, in the case of alginic acid, calcium chloride, strontium chloride, barium chloride, or aluminum chloride can be added in 0.01 to 5% by weight with respect to the weight of the medium, preferably 0.5 to 3% by weight.

For example, when a capsule including *bifidobacteria* is cultured, the *bifidobacteria* can be cultured and grown in the capsule, so that the number of the living *bifidobacteria* in the capsule is as large as several tens billion/g or more of the capsule. In addition, since living cells are cultured in the capsule, metabolites (e.g., bacteriocin, polysaccharides), are kept in the capsule, while such metabolites may be lost when bacteria is cultured in a tank and washed with water. Therefore, when *bifidobacteria* that has grown in the capsule is ingested in the form of the whole capsule, a more immediate and potent effect of improving intestinal disorders can be exhibited compared with the ingestion of a powder of freeze-dried bacteria. Furthermore, an effect of making the skin and the articulation smooth also can be provided.

In the capsule including living lactic bacteria, the lactic bacteria can be cultured and grown in the capsule. Therefore, when the capsule is used as a bioreactor of lactic acid fermentation, lactic acid can be produced with high efficiency, because there is not any contamination of lactic bacteria, and is easy to recover the lactic acid.

In the present invention, the cells or the tissues included in the capsule can grow in a desired medium. The capsule including the grown cells or tissues can be used for foods or the like. For example, lactic acid bacteria (*bifidobacteria*), ginseng tissues or the like are enclosed in a capsule and are grown in the capsule. After then, the capsules are added to fruit juice beverages, vegetable juice, health drinks, soybean milk, jelly, processed milk, yogurt, lactic acid bacteria beverages, fermented milk, carbonated drinks, near water, pudding, or the like, so as to produce foods containing the capsules of the present invention. In the present invention, "jelly" includes foods in a gel-type. The foods to which the capsules can be added are not limited to the above foods.

There is no particular limitation regarding the amount of the capsules added to foods, but 0.1 to 10 g with respect to 100 g of food is preferable, and 0.5 to 3 g is more preferable.

Next, the artificial seeds of the present invention will be described. The artificial seeds of the present invention can preferably be made into seamless soft capsules having a three-layered structure having the innermost layer, the inner layer covering the innermost layer and the outer layer covering the inner layer or a multi-layered structure having more than three layers. FIG. 1 shows a schematic cross-sectional view of the artificial seeds of the present invention. FIG. 1 is a diagram for the case of the three-layered structure. The innermost layer includes, for example, an adventitious embryo, which is a cell tissue. This innermost layer is filled with a liquid or gel that contains components necessary to maintain the life of the adventitious embryo and growth factor thereof. The inner layer is composed of an inner membrane (shown as "inner membrane (hardened oil membrane)" in FIG. 1) having hardened oil as the main component. This hardened oil membrane prevents water of the inclusion from evaporating, and suppresses oxygen permeation. The outermost layer is shown as "outer membrane (gelatin membrane)" in FIG. 1, and retains the physical strength and suppresses oxygen permeation.

In the description of various academic articles or patent documents, a single bead of calcium alginate gel may be referred to as "capsule". However, such a conventional capsule is completely different from the artificial seed of the present invention, as evident from the production method described later. Furthermore, the surface of the artificial seed capsules of the present invention is preferably dried, which shows that the artificial seed capsules of the present invention are different from the conventional capsule composed of wet alginic acid-gel.

As a cell tissue used in the present invention and included in the innermost layer, adventitious embryos, adventitious buds, multiple shoots, shoot apices, growing points, protocorm-like bodies, adventitious roots, capillary roots or the like can preferably be used. Virus-free tissues can be used as well.

In order to maintain the lives of cell tissues, it is preferable to suspend the cell tissues in, for example, water, a physiological saline, a buffer, a culture medium, or a liquid or a gel that contains necessary components to maintain an activity of differentiation (germination) of the cell tissues (hereinafter, collectively referred to as "medium"). A medium that is suitable for a desired plant and used by those skilled in the art are, for example, the basal medium of Murashige & Skoog (1962: hereinafter, referred to as "MS medium") or a modified medium thereof, although there is no limitation thereto. Furthermore, plant hormone, coconut milk, casein hydrolysate, yeast extract and the like, which are usually used in a culture medium, also can be added. In addition, in the case where it takes a long time to decompose the inner membrane and to germinate from the tissue after sowing, there is a possibility that a damage to the tissue is caused by microorganisms. In such a case, antibacterial agents can be added in order to suppress the growth of the microorganisms.

As the inner membrane, oil and fat containing hardened oil as the main component can preferably be used. "Containing hardened oil as the main component" means that the inner membrane is composed of only hardened oil or a mixture of hardened oil and other oil and fats so as to adjust the desired properties. A preferable inner membrane is a microbiologically degradable hardened oil that is solid at room temperature. "Hardened oil that is solid at room temperature" refers to hardened oil having a melting point of about 20° C. or more. The melting point may be 30° C. or more, 40° C. or more, or 50° C. or more. Hardened oil having a melting point of 20 to 50° C. is preferably used. What kind of the hardened oil to be used can be determined in view of the storage temperature, the sowing time or the like.

As the hardened oil, triglycerides, diglycerides or the like that contains fatty acids of medium carbon chain can be used. Specific examples thereof include, but are not limited to, butter, margarine, shortening, and cocoa butter.

It is necessary that this inner membrane is waterproof, not only to form a capsule enclosing an aqueous substance, but also to prevent from evaporating water of the innermost layer (aqueous phase) that contains cell tissues.

"Biodegradability" or "microbiologically degradable" means that the substance can be degraded or assimilated by microorganisms or other organisms when being sown in soil. When the hardened oil is degraded or assimilated, the inner membrane composed of the hardened oil is decomposed. Thus the barrier against a release of the tissue to outside of the capsule is removed, and the permeability of oxygen is increased, which activates the cell tissue to get out from the dormant state so that differentiation and growth of the tissue may occur.

It is preferable that the outer membrane is swollen with water and is biodegradable or microbiologically degradable, because a barrier against germination can be removed so that the cell tissues can be coming out form the capsule after the differentiation and growth of the cell tissue. Examples of the outer membranes that are biodegradable or microbiologically degradable include proteins, polysaccharides, and biodegradable plastics. These substances can be used alone or in combination of two or more.

Examples of the proteins include, but are not limited to, gelatin and collagen. These substances can be used alone or in combination of two or more.

As the polysaccharides, gel-forming polysaccharides are preferably used. Examples of such polysaccharides include, but are not limited to, agar, carrageenan, Arabian gum, gellant gum, xanthan gum, pectin, and alginic acid. These substances can be used alone or in combination of two or more.

Examples of biodegradable plastics include, but are not limited to, polylactic acid, polyhydroxybutyric acid, and a mixture thereof. These substances can be used alone or in combination of two or more.

Furthermore, if desired, properties of the outer membrane can be modified by adding saccharides, sugar alcohol, polyhydric alcohol, pullulan, chitosan or the like to the above-described biodegradable substances.

A particularly preferable outer membrane is gelatin, whose oxygen barrier properties can be increased after it is dried.

The artificial seed capsules of the present invention can have a structure of four or more layers, if desired. By selecting materials for the outer membrane, various properties can be given to the outer membrane. Furthermore, the surface of the artificial seed capsules may be coated with pharmaceuticals.

A general method for producing a three-layered seamless soft capsule has already been described above food application. For artificial seeds, for example, as the inclusion (the innermost layer) of the capsule, a suitable size of adventitious embryo which is obtained from a cell tissue (e.g., adventitious embryo) that is grown in a liquid medium or a solid medium and suspended in a medium can be used. As the inner membrane, hardened oil that is solid at room temperature can be used. As the outer membrane, a solution of biodegradable substance having an appropriate concentration (e.g., 22% gelatin solution) can be used. Using those components, the three-layered capsule can be produced by dropping a drop of capsule into a liquid using an apparatus provided with a triple tube nozzle. In this case, a pump is adjusted so that one adventitious embryo is put in the inner liquid in each capsule. Shaping and solidification of the capsule are performed in solidification oil, so that a capsule having a three-layered structure is produced. The solidification oil can be removed from the capsules formed, and then the capsules are subjected to drum drying, so that artificial seeds of the surface-dried capsule including adventitious embryos are obtained. The drying is performed at a low temperature so that the cell tissues do not die.

The particle size of the artificial seed capsule is 1 mm to 12 mm, depending on the size of the cell tissues. Preferably, the size is 3 to 10 mm. The number of the cell tissues to be enclosed in a capsule can range from one to several, depending on the size of the tissue. The number of the tissues can be determined so that the capsule has appropriate properties as the artificial seeds in view of the redifferentiation rate (germination rate). The number of cell tissues depends on the type of the plant but is preferably 1 to 4.

The thus obtained artificial seed capsules of the present invention can be stored for three months or more at room temperature in a dry barn or the like while retaining the germination ability. Therefore, there is no need of a special refrigerator or storage in low temperature water. If they are stored in a refrigerator at 10° C. or less, long term storage of 6 months or more can be achieved.

The capsulated artificial seed of the present invention can be a hollow seamless soft capsule encompassing a redifferentiable plant cell tissue (cell tissue). The capsule is composed of an inner membrane made of hardened oil and an outer membrane made of biodegradable gel (protein, polysaccharides) or biodegradable plastics, where the surface of the capsule (outer membrane) is dried. Such a composition of the capsule restricts oxygen supply to the inside of the capsule, which enables the cell tissue to survive in a dormant state in the capsule. Further, water is prevented from evaporating from the capsule and the capsule can be stored for two months or more at room temperature. Once the capsule is sown in soil, not only the outer membrane but also the hardened oil of the inner membrane can be degraded by water and the activities of the microorganisms in soil, thereby the permeability of oxygen can be increased and the cell tissue can be awakened from the dormant state and transfers to the germination state.

EXAMPLES

Hereinafter, the present invention will be described more specifically by way of examples, but the scope of the present invention is not limited thereby.

Example 1

Fruit Juice Beverage Containing Capsules That Includes Living *Bifidobacteria*

Two platinum loops colonies of *Bifidobacterium longum* JCM7050 were inoculated in 100 mL of a liquid skim milk medium containing 15% of skim milk, 0.4% of yeast extract, 3% of glucose, and pH 6.5. The cultivation were performed while shaking moderately at 60 rpm at 37° C. for 15 hours in an anaerobic container using ANAEROPACK (manufactured by Mitsubishi Gas Chemical Company, Inc.). Since the pH was decreased during the cultivation, the pH was kept at 5.5 with a 5M-NaOH aqueous solution, using an automatic pH regulator. The number of bacteria after 15 hours of cultivation was $2\times10^9$/ml measured by counting the colonies grown for 24 hours on a BL agar medium (manufactured by Nissui Pharmaceutical Co. Ltd.) under the anaerobic condition. This bacterium suspension was diluted 100 times with a skim milk medium having the same composition as above except that the 15% skim milk medium was treated with 0.01% pancreatin F (manufactured by Amano Pharmaceuticals) at 45° C. for 15 hours. The dilute was used as the inner liquid of the capsule. Hereinafter, the skim milk medium treated with the pancreatin is called as "pancreatin treated skim milk medium".

Next, capsules having a three-layered structure including this inner liquid (average particle size of 1.8 mm) were prepared according to the formulation shown in Table 1 by using a dropping method with a triple tube nozzle so as to produce seamless soft capsules. As the outer membrane, agar was used and shaping and solidification were performed in a solidification liquid.

TABLE 1

| Layer | Component | component ratio* (weight %) |
|---|---|---|
| Innermost layer | bifidobacteria liquid | 30 |
| inner layer | vitamin E oil | 30 |
| outermost layer | 2% agar solution | 40 |

*with respect to the total weight of the capsule

Then, 100 g of these capsules were put in 1 L of a pancreatin treated skim milk medium. The cultivation was performed with bubbling a mixed gas composed of 85% of nitrogen, 10% of hydrogen and 5% of carbon dioxide (manufactured by Sumitomo Seika Chemicals Co. Ltd.) at a flow rate of 100 ml/min, at 37° C. for 30 hours while stirring moderately at 50 rpm with a stirring blade and adjusting the pH to 5.5. After the cultivation, the number of living bacteria in the capsule was $3\times10^{10}$/g of the capsule (wet weight).

After the surfaces of the capsules were washed with sterile distilled water, the capsules were added in an amount of 2 g to 100 ml transparent muscat juice. Thus a muscat juice beverage containing capsules in which there are as many living *bifidobacteria* as 60 billions per 100 ml of muscat juice was prepared. The muscat juice beverage containing capsules including living *bifidobacteria* kept its transparency and tasted good, because there is no bad taste peculiar to *bifidobacteria*. Since the muscat juice beverage containing the capsules has a large number of living *bifidobacteria*, it is expected to have an effect of improving intestinal disorders.

Example 2

Vegetable Juice Containing Capsules that Includes Living Lactic Acid Bacterium

Lactic acid bacterium, *Lactococcus lactis* JCM7638, were plated and clutured on a CMG agar medium (0.5% of yeast extract, 0.5% of polypeptone, 0.5% of NaCl, 1% of glucose, and 2% of agar). One platinum loop of colonies were inoculated in 20 ml of a liquid skim milk medium of pH 6.5 including 12% of skim milk, 0.4% of yeast extract, 3% of glucose and was cultured stationary at 37° C. for 15 hours. The number of bacteria after 15 hours cultivation was $2\times10^9$/ml. This bacterium suspension was diluted 500 times with the same skim milk medium and was used as the inner liquid of the capsule.

Next, capsules (average particle size: 1.8 mm) having a three-layered structure and including this inner liquid were prepared in the same manner as described in Example 1.

Then, 100 g of the obtained capsules were put in 500 ml of a skim milk medium having the same composition as above except that the 12% skim milk aqueous solution that was treated with 0.01% protease P (manufactured by Amono pharmaceuticals) at 40° C. for 15 hours (hereinafter, referred to as "protease P-treated skim milk medium for lactic acid bacteria") was used. The capsules were cultured at 37° C. for 2 days while shaking at 50 rpm and adjusting the pH to 5.2 with a 5M-NaOH aqueous solution. The number of living bacteria in the capsule after the cultivation was $6\times10^{10}$/g of the capsule (wet weight), which indicated that the lactic acid bacteria were grown in the capsule significantly.

After the thus obtained capsules were washed with a sterile distilled water, and then the capsules were added in a ratio of 1 g/100 ml to vegetable juice. Although this vegetable juice contained a large amount of living lactic acid bacteria, it was not unsavory. The capsules were taken smoothly and tasted good. Thus, a large amount of lactic acid bacteria can be taken by drinking the vegetable juice, which was not thought to be possible before.

Example 3

Health Drink Containing Capsules that Includes Ginseng-Cultured Cell

First, 5 g (wet weight) of cell tissues of ginseng (Panax ginseng C.A. Meyer) that had been subjected to subculture in a Murashige-Skoog liquid medium (pH 5.6) containing 3% of sucrose and 1 mg/l of indole-3-acetic acid (IAA) were put in a 500 ml Erlenmeyer flask, followed by addition of 100 ml of the same medium, and then subjected to cultivation at 25° C. for two weeks while shaking at 120 rpm and thus a free cell cluster was obtained. Then, this free cell cluster was filtered with a nylon net having a hole size of 80 μm, and a fine cell cluster that passed through the nylon net was filtered with a nylon net having a hole size of 20 μm, and thus the cell cluster that was left on the net was collected. This cell cluster was suspended in an amount of 5 g (wet weight) in 100 ml of the Murashige-Skoog liquid medium having the same composition as above, and used as the inner liquid of the capsule.

The seamless soft capsules were prepared in the same manner as in Example 1 except that the cell suspension, which was the inner liquid, was vibrated by a vibrator during the feeding of the cell suspension. Then, 10 g of the obtained capsules including ginseng cells were collected and put in a 500 ml Erlenmeyer flask, and 100 ml of the Murashige-Skoog liquid medium having the same composition as above were added, and then subjected to cultivation at 25° C. at 50 rpm for three weeks. The ginseng cells were grown in the capsule and filled in the capsule. Then, 2 g of the capsules obtained after cultivation were washed with a sterile distilled water, and then added to 50 ml of a health drink that does not contain a ginseng extract to which 0.05 g of pectin was added in order to drift the capsules. Thus, a health drink containing capsules that include living ginseng cells was prepared. This health drink was not bitter or unsavory, taken smoothly and tasted good, although it contains living ginseng cells.

Example 4

Soybean Milk Containing Capsules That Includes Bacillus natto

First, to 500 ml of water, 100 g of pulverized soybean flour, 5 g of sucrose and 1 g of NaCl were added. The mixture was autoclaved at 121° C. for 30 minutes, followed by centrifugation so as to obtain a supernatant. Hereinafter, the supernatant is referred to as "soybean extract medium". Then, 10 ml of the soybean extract medium was put into a 50 ml Erlenmeyer flask, and one platinum loop of the colonies of *Bacillus natto* (*Bacillus subtilis* IFO13169) were inoculated. The *Bacillus natto* was cultured at 30° C. for 15 hours while shaking at 120 rpm. Whole culture broth was added to 90 ml of a soybean extract medium, and mixed uniformly so as to utilize this suspension as the inner liquid of the capsule.

Capsules were prepared in the same manner as in Example 1. One hundred grams of the obtained capsules were added to 400 ml of a soybean extract medium, and the capsules were cultivated at 30° C. for 24 hours at 100 rpm. The *Bacillus natto* were increased in the capsule during the cultivation and produced a viscous substance. The number of the bacteria was $3\times10^9$/g of the capsule (wet weight). Then, 3 g of these capsules were washed with distilled water and added to 100 ml of soybean milk. This soybean milk containing the capsules did not smell of *Bacillus natto* and tasted good for drink. This beverage allows *Bacillus natto* and a viscous substance to be taken together with soybean milk.

Example 5

Method for Cultivating Capsulated Bifidobacteria

Capsules including *Bifidobacterium longum* JCM7050 prepared in the same manner as in Example 1, were packed in a 100 ml of cylindrical column provided with a jacket for temperature adjustment. Then, 1 L of pancreatin-treated skim milk was put into an external medium bath, and the medium was allowed to flow from the lower portion of the column packed with the capsule to the upper portion at 10 ml/min and returned to the medium bath again for circulation. The pH in the medium bath was kept at 5.5 with 10M ammonium aqueous solution using an automatic pH regulator. During the circulation, a mixed gas composed of 85% of nitrogen, 10% of hydrogen and 5% of carbon dioxide (manufactured by Sumitomo Seika Chemicals Co. Ltd.) was blown into the medium bath in order to maintain an anaerobic condition. The mixed gas was blown at 100 ml/min for the first 12 hours, and at 20 ml/min from the $12^{th}$ hour to the $30^{th}$ hour. After circulation at 37° C. for 30 hours, the number of the Bacteria was as high as $5\times10^{10}$/g of the capsule.

This culture method using column packed with capsules allows *bifidobacteria* to be cultured to a high density in the capsule without accepting any physical damages, and reduces the possibility of contamination. Furthermore, the capsules are not broken when the capsules are collected, and can be conveyed with the column to a place where they are mixed with foods. Therefore, the handling during and after cultivation is very easy, so that this method is suitable industrially for the culturing of *bifidobacteria* in the capsule.

Example 6

Capsulation and Cultivation of Freeze-Dried Bacteria

*Bifidobacterium longum* JCM7050 was subjected to anaerobic culture in a skim milk medium in the same manner as in Example 1. After cultivation, the bacteria were collected by centrifugation at 4° C., 8000 rpm for 20 minutes. Sterilized distilled water was added to the pellet in an amount 10 times larger than that of the bacteria, followed by stirring and dispersion and then the bacteria were freeze-dried. When the freeze-dried bacteria were subjected to cold storage in an airtight container that was made anaerobic by filling Anaero-Pack therein, the bacteria were stored very stable. Then, 0.1 g of the freeze-dried bacteria were collected and suspended in a 1 L of a skim milk medium and used as the inner liquid of the capsule. The number of the bacteria in this suspension was $5\times10^7$/ml.

Next, seamless soft capsules (average particle size of 3.5 mm) containing this inner liquid were prepared according to the formulation shown in Table 2 by dripping in the air.

TABLE 2

| Layer | Component | constitution ratio* (weight %) |
|---|---|---|
| innermost layer | bifidobacteria liquid | 30 |
| inner layer | Vitamin E oil | 30 |
| outermost layer | 4% sodium alginate solution | 40 |
| Solidification liquid | 3% calcium chloride aqueous solution | |

*with respect to the total weight of the capsule

Then, 100 g of the obtained capsules were put into 1 L of a pancreatin-treated skim milk medium, and were cultivated at 37° C. for 2 days while shaking and adjusting the pH to 5.5 with a 5M NaOH aqueous solution. The number of living bacteria in the capsule after the cultivation was $2\times10^{10}$/g of the capsule (wet weight), which indicates growth of the bacteria in the capsule.

Example 7

Lactic Acid Bacteria Beverage Containing Capsules That Includes Living *Bifidobacteria*

Lactic acid bacterium, *Lactococcus lactis* JCM7638, was cultured on a CMG agar medium (0.5% of yeast extract, 0.5% of polypeptone, 0.5% of NaCl, 1% of glucose, and 2% of agar) so that colonies of the bacteria were obtained. One platinum loop of the colonies were collected and were inoculated in 20 ml of a liquid skim milk medium of pH 6.5 including 12% of skim milk, 0.4% of yeast extract, 3% of lactose and were cultured stationary at 37° C. for 15 hours. The number of bacteria was $6 \times 10^9$/ml.

The whole culture broth was centrifuged at 4° C., 8,000×g for 20 minutes, and the supernatant was disposed off. To the bacterial pellet, 40 ml of a physiological saline were added, stirred with a vortex, followed by centrifugation at 8,000×g for 20 minutes, and the bacteria were collected. The same washing operation was repeated once again and washed bacteria were obtained. To the pellet of the washed bacteria, transparent apple juice was added in an amount of 40 ml, followed by dispersing the bacteria uniformly with a vortex. Then, 0.5 ml of the apple juice in which the bacteria were suspended uniformly was added to 100 ml of transparent apple juice. The number of the bacteria in the apple juice was $1 \times 10^7$/ml. Appearance of the apple juice was substantially transparent.

Separately, capsules including *bifidobacteria* were prepared in the same manner as in Example 1. Two grams of the capsules including *bifidobacteria* were added to 100 ml of the lactic acid bacteria-suspended apple juice obtained above. The number of the living *bifidobacteria* included in the capsule was 30 billion/g of the capsule. The apple juice containing the living lactic acid bacteria and the capsules including the living *bifidobacteria* can satisfy the definition of lactic acid bacterium beverage according to the standard of "ministerial ordinance regarding milk". However, the lactic acid bacterium beverages of the present invention is totally different from conventional lactic acid bacterium beverages in that the beverage of the present invention is substantially transparent, 60 billion of living *bifidobacteria* can be ingested per 100 ml, and can be drunk smoothly.

Example 8

Artificial Seed Capsules Containing Carrot Adventitious Embryo

Cell culture and adventitious embryos of carrots were prepared from roots of carrots according to a method described in "Plant cell tissue culture" at pp. 91 to 104 (1979, edited by Harada and Komane, published by Rikogakusha). Adventitious embryos were grown in a liquid medium and screened with nylon meshes having a hole size of 500 μm and 850 μm, so as to obtain adventitious embryos having a size of 500 μm to 850 μm. The obtained adventitious embryos had a shape ranging from a heart shape to a torpedo shape. These adventitious embryos were suspended in a MS medium containing 0.2% of chitosan, and this suspension was used as the inclusion of the capsules.

Capsulation of the adventitious embryo was performed by a method of dropping the drop of capsule in a liquid. In this method, hardened oil (PHARMASOL B-115 (glycerin fatty acid ester ($ROCOCH_2$—$CH(OCOR)$—$CH_2OCOR$, $R = C_{12-18}$)) manufactured by NOF CORPORATION) that is composed of triglyceride and has a melting point of 32° C. was used as the inner layer. A 22% gelatin solution was used as the outer layer. Using an apparatus for producing seamless soft capsules provided with a triple tube nozzle, artificial seed capsule were prepared while a feed pump of the adventitious embryo was adjusted so that one adventitious embryo could be put in a liquid in each capsule. Shaping from the drop of capsule and solidification of the capsule were performed in solidification oil, so as to obtain capsules having a three-layered structure. The solidification oil was removed from the obtained capsules, and then the capsules were subjected to drum drying so as to obtain the surface-dried artificial seed capsules including an adventitious embryo. The particle size of the capsule after drying was 7 mm.

Separately, as a comparative example, carrot adventitious embryos embedded in an alginate gel beads (Comparative Example 1) were prepared. More specifically, the adventitious embryos that were prepared and screened in Example 8 were suspended in a MS medium containing 3% (w/v) sodium alginate, and the suspension was dropped in a 50 mM calcium chloride solution. By this method, the adventitious embryos were embedded in a calcium alginate gel beads (particle size: 5 mm). These are equivalent to those reported as the conventional artificial seeds.

Preservation and Germination Test

The artificial seed capsules containing adventitious embryos (Example 8) of the present invention and calcium alginate gel beads in which an adventitious embryo is embedded (Comparative Example 1) were preserved in an incubator at 20° C. and a humidity of 65% for three months. On Day 3 of the storage, the calcium alginate gel beads were fairly dried and the particle size of the beads was shrinked. The adventitious embryos in the calcium alginate gel beads also became dry after one week, and were dried up. On the other hand, there was no change in the appearance of the artificial seed capsules even after one week.

One month, two months and three months after the preparation of the artificial seed capsules, 100 grains each were sown in a depth of 2 cm from the surface in a pot filled with soil of a field and sprinkled with water. The soil was not subjected to sterilization. After the sowing, the pots were put in an incubator at 25 ° C. and illuminated at 3000 Lux for 16 hours per day, and were sprinkled with water once in two days for growth. Table 3 shows the results of counting the number of germinations after three weeks from the seeding.

TABLE 3

Results of germination tests of carrot artificial seed capsules

| | Storage period | | | |
|---|---|---|---|---|
| | immediately after preparation | one month | two months | three months |
| Example 8 | 95 | 75 | 72 | 68 |
| Com. Ex. 1 | 96 | 0 | 0 | 0 |

As shown in Table 3, the germination rates of those immediately after the preparation were substantially equal between Example 8 and Comparative Example 1. However, when the artificial seeds were stored more than one month, the conventional artificial seeds of Comparative Example 1 did not germinate at all. On the other hand, for the artificial seed capsules of the present invention, the germination rate was as high as 68% even after three months storage.

These results indicated that the adventitious embryos included in the capsule of the present invention were far superior to the conventional artificial seeds embedded in the calcium alginate gel beads with respect to the storage stability of the artificial seeds.

Example 9

Artificial Seed Capsules Including Strawberry Leaf Bud

Shoot apex tissues extracted from cultivated strawberries were put into a MS medium containing 10 g/l of sucrose and 2 g/l of gellant gum as a gelling agent, and cultured in a dark place at 25° C. for 14 days. Then the tissue was transferred to a MS liquid medium containing 0.2 mg/l of benzyladenine and 10 g/l of sucrose, and cultivated using a rotational shaker at 150 rpm while irradiating at 25° C. at 2000 Lux for 16 hours per day. After 30 days of cultivation, the obtained leaf buds were screened using nylon meshes having a hole size of 1 mm to 1.7 mm, so that leaf buds having a size of 1 to 1.7 mm were obtained. The obtained leaf buds were suspended in a MS liquid medium that did not contain hormones, and this suspension was used as the inclusion of the capsule.

Capsulation was performed in the same manner as in Example 8 except that the flow rate of the pump supplying the leaf bud suspension was regulated. The surface of the obtained capsules was dried to obtain the artificial seed capsules including strawberry leaf buds. The particle size of the capsule after drying was 8 mm.

Separately, as a comparative example, strawberry leaf buds were embedded by calcium alginate gel beads (Comparative Example 2). The strawberry leaf buds were prepared and screened in the same manner as in Example 9 and the calcium alginate gel beads (particle size: 5 mm) embedding the strawberry leaf buds were prepared in the same manner as in Comparative Example 1. The calcium alginate gel beads embedding the strawberry leaf buds (Comparative Example 2) corresponds to the conventional artificial seeds.

The storage and the germination tests of the obtained artificial seed capsules including strawberry leaf buds (Example 9) and the calcium alginate gel bead embedding strawberry leaf buds (Comparative Example 2) were performed in the same manner as in Example 8. Table 4 shows the results.

TABLE 4

Results of germination tests of strawberry artificial seeds

| | Storage period | | | |
|---|---|---|---|---|
| | Immediately after preparation | One month | two months | Three months |
| Example 9 | 91 | 71 | 68 | 63 |
| Com. Ex. 2 | 94 | 0 | 0 | 0 |

The figures indicate the number of germinations when 100 grains were sown.

As shown in Table 4, the germination rates of those immediately after the preparation were substantially equal between Example 9 and Comparative Example 2. However, when the artificial seeds were stored more than one month, the conventional artificial seeds of Comparative Example 2 did not germinate at all. On the other hand, the artificial seed capsules of the present invention germinate at a high rate, and the germination rate was kept as high as 60% or more even after three months storage.

These results indicated that the storage stability of the artificial seed capsules of the present invention were far superior to the conventional artificial seeds, such as calcium alginate gel bead.

Example 10

Artificial Seed Capsules Including a Protocorm-Like Body of *Orchis graminifolia*

The protocorm-like bodies formed from the flower stalk lateral bud of *Orchis graminifolia* with white flowers and yellow lips were screened using nylon meshes having a hole size of 1.5 mm and 3 mm so that protocorm-like bodies having a size of 1.5 to 3 mm were obtained. The obtained protocorm-like bodies were suspended in a medium of pH 5.6 containing 6 g/1 of a HYPONeX fertilizer (N/P/K =6.5: 6:19), 15 g/l of sucrose and 0.2% of chitosan. This suspension was used as the inclusion of the three-layered capsule.

Capsulation was performed in the same manner as in Example 8 except that the pump supplying this protocorm-like body suspension was adjusted so that one protocorm was included in one capsule. The surface of the obtained capsules was dried, and thus surface-dried artificial seed capsules including the protocorm-like bodies of *Orchis graminifolia* were obtained. The particle size of the capsule after drying was 9 mm.

After these artificial seeds were stored for 2 months in a dark place at 15° C., 100 grains each were sown in a depth of 2 cm from the surface in a pot filled with soil of a field and sprinkled with water. The soil was not subjected to sterilization. After the sowing, the pots were put in an incubator at 25° C. and illuminated at 3000 Lux for 16 hours per day, and were sprinkled with water once in two days for growth. When the number of germinations was counted after two months storage, it was found that 63 of the 100 grains germinated.

Examples 11 to 16

The adventitious embryos, apical buds and adventitious roots of the plants shown in Table 5 were created and capsulated in the same manner as in Example 8, and the surface of the capsules was dried. After the capsules were stored in an incubator at 20 ° C. and a humidity of 65% for three months, 100 grains each were sown in pots in the same manner as in Example 8 for growth for 1 to 3 months in the same manner as in Example 8. Then, germination was observed. Table 5 shows the results.

TABLE 5

Results of germination test of artificial seed capsules including various plants

| Example | Plant | cell tissue | particle size (mm) | Number of germinations |
|---|---|---|---|---|
| 11 | *Asparagus* | Adventitious embryo | 7 | 71 |
| 12 | *Cyclamen* | Adventitious embryo | 8 | 68 |
| 13 | Easter lily | Apical bud | 9 | 53 |
| 14 | *Dianthus caryophyllus* | Adventitious embryo | 8 | 62 |
| 15 | Rose | Adventitious root | 9 | 51 |
| 16 | *Cryptomeria japonica* | Adventitious root | 10 | 37 |

The results of Table 5 also indicate that the storage stability of the artificial seed capsules of the present invention is excellent.

Industrial Applicability

The capsule of the present invention is constituted so that living cells or tissues can grow even in the capsule and cannot be dissolved by gastric acid. Therefore, particularly when lactic acid bacteria (including *bifidobacteria*) are included, a large amount of living bacteria can be delivered to the intestines so that a rapid and potent improvement of an intestinal disorders can be exhibited. Furthermore, the artificial seed capsule including a redifferentiable plant cell tissue of the present invention has high storage stability in a dry state at room temperature and when being sown in soil, the capsule membrane is swollen and decomposed by microbial activities and thus germinates rapidly. The present invention can be applied to a wide range fields such as agriculture, forestry, horticulture and floriculture in combination with a cloning technique or a virus free technique.

The invention claimed is:

1. An artificial seed for maintaining an activity of differentiation of a plant cell or a plant tissue, wherein
    the artificial seed is formed of a seamless soft capsule with a structure of three layers, the structure of three layers consisting of an innermost layer, an inner layer covering the innermost layer, and an outer layer covering the inner layer,
    the innermost layer consists of the plant cell or the plant tissue and an aqueous liquid medium that contains a component to maintain an activity of differentiation of the plant cell or the plant tissue, the plant cell or the plant tissue is suspended in the aqueous liquid medium, the plant cell or the plant tissue is selected from the group consisting of adventitious embryos, adventitious buds, multiple shoots, shoot apices, growing points, protocorm-like bodies, adventitious roots, and capillary roots,
    the inner layer is formed by an inner membrane consisting essentially of hardened oil that is solid at room temperature, the inner membrane is to prevent from evaporating water of the innermost layer, and
    the outer layer is formed of a biodegradable outer membrane having an oxygen barrier property after dried.

2. The artificial seed according to claim 1, wherein the outer membrane is dried.

3. The artificial seed according to claim 1, wherein the hardened oil is microbiologically degradable.

4. The artificial seed according to claim 1, wherein the outer membrane is a microbiologically degradable outer membrane selected from the group consisting of protein, polysaccharides, and biodegradable plastics.

5. The artificial seed according to claim 4, wherein the inner membrane is microbiologically degradable hardened oil that is solid at room temperature.

6. The artificial seed according to claim 3, wherein the outer membrane is a microbiologically degradable outer membrane selected from the group consisting of protein, polysaccharides, and biodegradable plastics.

7. An artificial seed comprising a seamless capsule, the seamless capsule comprising:
    an innermost layer consisting of a plant cell or a plant tissue and an aqueous liquid medium that contains a component to maintain an activity of differentiation of the plant cell or the plant tissue, the plant cell or the plant tissue is suspended in the aqueous liquid medium, the plant cell or the plant tissue is selected from the group consisting of adventitious embryos, adventitious buds, multiple shoots, shoot apices, growing points, protocorm-like bodies, adventitious roots, and capillary roots;
    an inner layer covering the innermost layer, the inner layer consisting essentially of a lipophilic material, the inner layer is to prevent from evaporating water of the innermost layer; and
    an outer layer covering the inner layer, the outer layer comprising a biodegradable material and having an oxygen barrier property after dried.

8. The artificial seed according to claim 7, wherein the outer layer is dried.

9. The artificial seed according to claim 7, wherein the lipophilic material consists essentially of a hardened oil.

10. The artificial seed according to claim 9, wherein the hardened oil is solid at room temperature.

11. The artificial seed according to claim 7, wherein the biodegradable material is selected from the group consisting of protein, polysaccharides, and biodegradable plastics.

12. The artificial seed according to claim 7, wherein the seamless capsule has a particle size from 0.1 mm to 10 mm.

13. The artificial seed according to claim 7, wherein the seamless capsule has a particle size from 0.2 mm to 8 mm.

14. The artificial seed according to claim 7, wherein the seamless capsule has a particle size of 4 mm or less.

15. The artificial seed according to claim 1, wherein the hardened oil has a melting point of 35° C. or less.

* * * * *

UNITED STATES PATENT AND TRADEMARK OFFICE
CERTIFICATE OF CORRECTION

| | |
|---|---|
| PATENT NO. | : 8,859,853 B2 |
| APPLICATION NO. | : 11/210424 |
| DATED | : October 14, 2014 |
| INVENTOR(S) | : Asada et al. |

Page 1 of 1

It is certified that error appears in the above-identified patent and that said Letters Patent is hereby corrected as shown below:

In the Specification

Column 14, Line 57, Insert --The figures indicate the number of germinations when 100 grains were sown.-- below Table 3.
Column 16, Line 64, Insert --The number of germinations indicates the number when 100 grains were sown.-- below Table 5.

Signed and Sealed this
Eighteenth Day of August, 2015

Michelle K. Lee
*Director of the United States Patent and Trademark Office*